(12) United States Patent
Vik et al.

(10) Patent No.: US 10,675,483 B2
(45) Date of Patent: Jun. 9, 2020

(54) RADIATION THERAPY PLANNING OPTIMIZATION AND VISUALIZATION

(71) Applicant: KONINKLIJKE PHILIPS N.V., Eindhoven (NL)

(72) Inventors: Torbjoern Vik, Hamburg (DE); Harald Sepp Heese, Hamburg (DE); Daniel Bystrov, Hamburg (DE); Juergen Weese, Norderstedt (DE); Christoph Neukirchen, Aachen (DE); Alfonso Agatino Isola, Eindhoven (NL); Matthieu Frederic Bal, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 577 days.

(21) Appl. No.: 15/512,896

(22) PCT Filed: Sep. 9, 2015

(86) PCT No.: PCT/IB2015/056884
§ 371 (c)(1),
(2) Date: Mar. 21, 2017

(87) PCT Pub. No.: WO2016/046683
PCT Pub. Date: Mar. 31, 2016

(65) Prior Publication Data
US 2018/0078786 A1 Mar. 22, 2018

Related U.S. Application Data

(60) Provisional application No. 62/053,402, filed on Sep. 22, 2014.

(51) Int. Cl.
*A61N 5/10* (2006.01)
*G16H 20/40* (2018.01)
(Continued)

(52) U.S. Cl.
CPC .......... *A61N 5/1036* (2013.01); *A61N 5/103* (2013.01); *A61N 5/1031* (2013.01);
(Continued)

(58) Field of Classification Search
CPC ..... G06F 19/3456; G16H 20/40; G16H 50/30
See application file for complete search history.

(56) References Cited

U.S. PATENT DOCUMENTS

| 3,871,579 A | 3/1975 | Inamura |
| 4,455,609 A | 6/1984 | Inmura et al. |

(Continued)

FOREIGN PATENT DOCUMENTS

| JP | 2002172180 A | 6/2002 |
| JP | 2016521587 A | 7/2016 |

OTHER PUBLICATIONS

Romeijn,J., et al., "A column generation approach to radiation therapy treatment planning using aperture modulation", SIAM J. Optim., 15(3), 838-862, 2005.
(Continued)

*Primary Examiner* — Dani Fox
*Assistant Examiner* — Soorena Kefayati

(57) ABSTRACT

A radiation planning system includes a predictor-corrector optimizer unit which computes a predicted dose based on a collection of control points with a current approximate dose, each control point with a corresponding set of leaf positions, and determines an additional control point with a corresponding set of leaf positions based on a difference of the predicted fluence and the current approximate fluence through a least cost or shortest path in a layered graph structure of realizable leaf positions. Tools are described to help a planner to evaluate the effect of parameter changes to the current plan based on an identified zone of influence. The planner interactively views the current plan based on a
(Continued)

visualization of the plan objectives and correlations between the objectives.

17 Claims, 6 Drawing Sheets

(51) Int. Cl.
*G16H 50/30* (2018.01)
*G06F 19/00* (2018.01)

(52) U.S. Cl.
CPC ........... *A61N 5/1045* (2013.01); *G16H 20/40* (2018.01); *G16H 50/30* (2018.01); *A61N 5/1039* (2013.01); *G06F 19/3456* (2013.01)

(56) References Cited

U.S. PATENT DOCUMENTS

| | | | |
|---|---|---|---|
| 6,314,159 B1* | 11/2001 | Siochi | A61N 5/1042 |
| | | | 250/492.3 |
| 6,366,798 B2 | 4/2002 | Green | |
| 6,385,477 B1* | 5/2002 | Werner | A61N 5/103 |
| | | | 378/4 |
| 6,449,335 B1* | 9/2002 | Siochi | A61N 5/1042 |
| | | | 378/147 |
| 6,853,705 B2* | 2/2005 | Chang | G21K 1/046 |
| | | | 378/65 |
| 7,110,808 B2 | 9/2006 | Adair | |
| 7,831,018 B1* | 11/2010 | Nord | A61N 5/103 |
| | | | 378/65 |
| 8,073,104 B2 | 12/2011 | Yan et al. | |
| 8,487,269 B2 | 7/2013 | Amies et al. | |
| 8,658,992 B2 | 2/2014 | Otto | |
| 8,913,716 B2 | 12/2014 | Sobering et al. | |
| 9,044,602 B2* | 6/2015 | Kilby | A61N 5/1031 |
| 9,067,064 B2* | 6/2015 | Jiang | A61N 5/1031 |
| 9,393,442 B2 | 7/2016 | Isola et al. | |
| 2003/0212325 A1 | 11/2003 | Cotrutz et al. | |
| 2004/0087254 A1 | 5/2004 | Shendon et al. | |
| 2004/0190680 A1* | 9/2004 | Chang | A61N 5/1042 |
| | | | 378/65 |
| 2005/0148841 A1* | 7/2005 | Kamath | A61N 5/103 |
| | | | 600/407 |
| 2006/0256915 A1* | 11/2006 | Otto | A61N 5/1031 |
| | | | 378/65 |
| 2008/0242969 A1* | 10/2008 | Sayeh | A61B 6/032 |
| | | | 600/407 |
| 2008/0278495 A1 | 11/2008 | Minamide et al. | |
| 2008/0285719 A1* | 11/2008 | Nord | A61N 5/103 |
| | | | 378/152 |
| 2009/0041188 A1* | 2/2009 | Keall | A61N 5/1042 |
| | | | 378/65 |
| 2009/0213991 A1* | 8/2009 | Brown | A61N 5/103 |
| | | | 378/65 |
| 2009/0225942 A1* | 9/2009 | Shepard | A61N 5/1042 |
| | | | 378/65 |
| 2010/0054410 A1* | 3/2010 | Nord | A61N 5/1031 |
| | | | 378/65 |
| 2011/0006215 A1* | 1/2011 | Van Heteren | A61N 5/1031 |
| | | | 250/453.11 |
| 2011/0091014 A1* | 4/2011 | Siljamaki | A61N 5/1031 |
| | | | 378/65 |
| 2011/0091015 A1* | 4/2011 | Yu | A61N 5/1047 |
| | | | 378/65 |
| 2012/0065489 A1* | 3/2012 | Nord | A61N 5/1036 |
| | | | 600/407 |
| 2013/0034208 A1 | 2/2013 | Heid et al. | |
| 2013/0077751 A1* | 3/2013 | Gunawardena | A61N 5/1047 |
| | | | 378/65 |
| 2013/0083004 A1* | 4/2013 | Nord | A61N 5/1031 |
| | | | 345/419 |
| 2013/0085343 A1* | 4/2013 | Toimela | A61N 5/1031 |
| | | | 600/300 |
| 2013/0187062 A1* | 7/2013 | Nord | A61N 5/1036 |
| | | | 250/492.1 |
| 2014/0105355 A1* | 4/2014 | Toimela | A61N 5/103 |
| | | | 378/41 |
| 2017/0296840 A1* | 10/2017 | Bokrantz | A61N 5/1045 |

OTHER PUBLICATIONS

Cambazard, H. et al., "A shortest path-based approach to the multileaf collimator sequencing problem", Discrete Applied Mathematics, Sep. 2, 2011, vol. 160, Nr: 1, pp. 81-99.

Carlsson, F., "Combining segment generation with direct step and shoot optimization in intensity modulated radiation therapy", Medical Physics, Aug. 7, 2008, vol. 35, Nr: 9, p. 3828-3838.

* cited by examiner

RADIATION THERAPY PLANNING OPTIMIZATION AND VISUALIZATION

CROSS-REFERENCE TO PRIOR APPLICATIONS

This application is the U.S. National Phase application under 35 U.S.C. § 371 of International Application Serial No. PCT/IB2015/056884, filed on Sep. 9, 2015, which claims the benefit of U.S. application Ser. No. 62/053,402, filed on Sep. 22, 2014. These applications are hereby incorporated by reference herein.

The following relates generally to external radiation therapy planning. It finds particular application in conjunction with radiation therapy plan construction, optimization and visualization, and will be described with particular reference thereto. However, it will be understood that it also finds application in other usage scenarios and is not necessarily limited to the aforementioned application. For example, the following can be used to deliver selected radiation doses to target regions in various industrial applications such as disinfecting, polymer burning, changing electrical, mechanical, or chemical properties and the like, to selected regions of manufactured products including internal regions even without physical access.

External Beam Radiation Therapy (EBRT) plans are constructed based on machine characteristics of the linear particle accelerator (LINAC) and information of each individual patient. For each patient case, a plan is created that contains a machine configuration needed to deliver, within the possibilities of a particular machine, therapeutic radiation. The goal of the radiation is to damage the tumor cells while minimizing radiation doses to organs-at-risk (OARs).

External beam radiation delivery (EBRT) devices such as a LINAC typically irradiate from different directions to minimize the dose to organs at risk. Different irradiation types are used. For example, most used is photon, and alternatives are electrons, protons, heavy ions. The shape of the radiation beam can be controlled with a multi-leaf collimator (MLC). The MLC includes pairs of leaves of radiation blocking material which are positionable within machine constraints and controlled by a controller. One set of leaf positions for both the left and right leafs of a beam is typically referred to as a control point (CP). The openings formed by all the control points at a specific beam position is in radiotherapy planning systems often represented by a fluence plane orthogonal to the radiation beam. Treatment planning systems contain algorithms that compute the three dimensional dose distribution resulting from a certain machine configuration. The density information of the patient is needed by these dose engines, and the density information is typically derived from a CT image.

In Intensity Modulated Radiation Therapy (IMRT) radiation is delivered in a step and shoot or a continuous mode. In step and shoot mode, the LINAC only delivers dose when the machine is configured according to a specific control point. When transitioning between two control points no dose is delivered. In a continuous dose delivery mode, the machine continuously transitions between CPs while continuously delivering dose.

The inverse planning techniques for IMRT that find the machine configuration that meets certain dose distribution criteria have in common that the optimal radiation dose solution is defined by a set of objectives. One type of inverse planning techniques uses a column generation (CG) approach with a heuristic algorithm that sequentially creates the CPs but does not perform a refinement of the existing control points. The CPs can be strongly sub-optimal possibly due to non-convexity of an objective function. The CG approach does have the advantages of direct fulfilment of machine constrains and that each CP is a global optimum with respect to minimizing a difference between a reference dose and a planned delivered dose.

An alternative technique is the Aperture Shape Optimization (ASO) approach that uses a complete set of CPs and improves an objective function through the derivative of a displacement of each leaf position with respect to the objective function. However, the ASO approach is a local refinement method and therefore dependent upon the selection of a starting point. The ASO approach is also slow to converge, can converge to local optima, and typically has difficulty fulfilling the machine constraints.

The ideal dose distribution and input for the inverse planning algorithms is most often defined by a set of objectives. An objective is typically a function of the dose in a region of interest and a weighting factor. The regions of interest used by the objectives include the target and organs at risk regions. Planning involves making tradeoffs between competing objectives. For example, delivering dose to a tumor may include delivering some radiation to a healthy OAR. A set of objectives can include multiple targets and/or multiple OARs.

The tradeoff in a radiation therapy (RT) plan between the dose delivered to the OAR and target volumes is typically made through a trial and error process. A RT planning device has as input the objectives and outputs the machine settings resulting in a planned dose in a black box type operation which can take minutes with each processing. A healthcare professional reviews the outputted dose distribution and changes the objective function by adding or removing objectives, adjusting weights or parameters of the objectives and reruns the IMRT inverse planning algorithm. The planned delivered dose is often visualized through isodose curves superimposed on the planning image. The planner typically compares different outputs to gain some understanding of the trade-offs and how changes to the inputs affect the output, a time consuming practice.

The RT planning device typically provides no information concerning the relationships of the objectives or the interplay between the different objectives. Furthermore, inverse planning algorithms are complex and can have difficulty with local minima. For example, the planner can change the set of objectives with a seemingly minor effect on the plan. In other words, it is often not clear to the planner what changes in the input can produce meaningful differences.

This trial and error approach can be found in intensity modulated radiation therapy (IMRT) in fluence map optimization (FMO), direct machine parameter optimization (DMPO), and volumetric modulated arc therapy (VMAT) inverse planning approaches.

The following discloses a new and improved radiation delivery planning optimization and visualization approaches which addresses the above referenced issues, and others.

In accordance with one aspect, a method of radiation delivery planning includes receiving a radiation therapy plan including a current dose $d_{curr}$ resulting from a collection of control points, each control point with a corresponding set of leaf positions for a multi-leaf collimator. The control points can be combined into a set of fluence planes with discrete values, $x_{curr}$. A relation between fluence planes values x and the three dimensional dose volume d is needed to compute the derivatives of the objective function O versus changes in the fluence planes:

$$\frac{\partial O}{\partial x} = \frac{\partial O}{\partial d}\frac{\partial d}{\partial x}.$$

An additional control point with a corresponding set of leaf positions is determined by a corrective mapping of a difference of the current approximate fluence planes values $x_{curr}$ and the predictive fluence plane values $x^*$ through a least cost or shortest path in a layered graph structure of paired leaf positions for each leaf pair. The resulting control point with corresponding set of leaf positions is added to the collection of control points, often followed by a segment weight optimization to adjust the weights of the individual control points.

In accordance with another aspect, a system for radiation delivery planning includes a control point manager unit, a prediction unit and a correction unit. The control point manager unit is configured to receive a radiation therapy plan which includes a collection of control points, each control point with a corresponding set of leaf positions for a multi-leaf collimator, and $x_{curr}$ is derived from these control points. The prediction unit is configured to calculate a predictive set of fluence planes values $x^*$. The correction unit is configured to select a control point and determine an alternative set of leaf positions by a corrective mapping of a difference of the current approximate fluence planes values and the predictive fluence planes values, $x^*-x_{curr}$, through a least cost or shortest path in a layered graph structure of leaf positions for that control point. Optionally the shortest path can be restricted to those leaf positions that are within a given range of the positions in the original control point. The control point manager unit is further configured to add the determined alternative set of leaf positions to the control point. With or without intermediate segment weight optimization a condition can be defined to either accept the new set of leaf positions or keep the old positions as a function of the relative improvement of the objective function.

In accordance with another aspect, a method of radiation delivery planning includes receiving a change in an objective function $O(d; \theta_0)$ caused by the change of a radiation plan parameter $\theta$. Where $\theta_0$ is the current value of the radiation plan parameter $\theta$. A zone of influence in the dose space is identified from the change in the parameter based on a function:

$$\frac{\partial O}{\partial \theta}.$$

In accordance with another aspect, a method of radiation delivery planning includes receiving a radiation therapy plan which includes dose voxels d and plan objectives O. The plan objectives are correlated. A diagram is constructed such as a graph or pivot table which visualizes the correlation between the plan objectives. The constructed diagram is displayed on a display device.

The advantages of the aspects described are:

One advantage is the determination of the leaf positions in a control point taking directly all machine requirements into account.

Another advantage is a better and faster determination of the preferred tradeoff between the different objectives of radiation delivery plans including RT plans.

Another advantage resides in tools which provide a better understanding of individual RT plans to a radiation therapy planner.

Another advantage resides in a column generation (CG) approach to RT planning which iteratively refines the CPs.

Another advantage resides in visualization for a planner of the potential impact of proposed RT plan parameter changes.

Another advantage resides in visualization for a planner of interplays between the RT plan objectives.

Still further advantages will be appreciated to those of ordinary skill in the art upon reading and understanding the detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of a radiation delivery planning optimization and visualization system.

FIG. 2 schematically illustrates one embodiment of a predictor-corrector optimizer unit.

Figure 5:
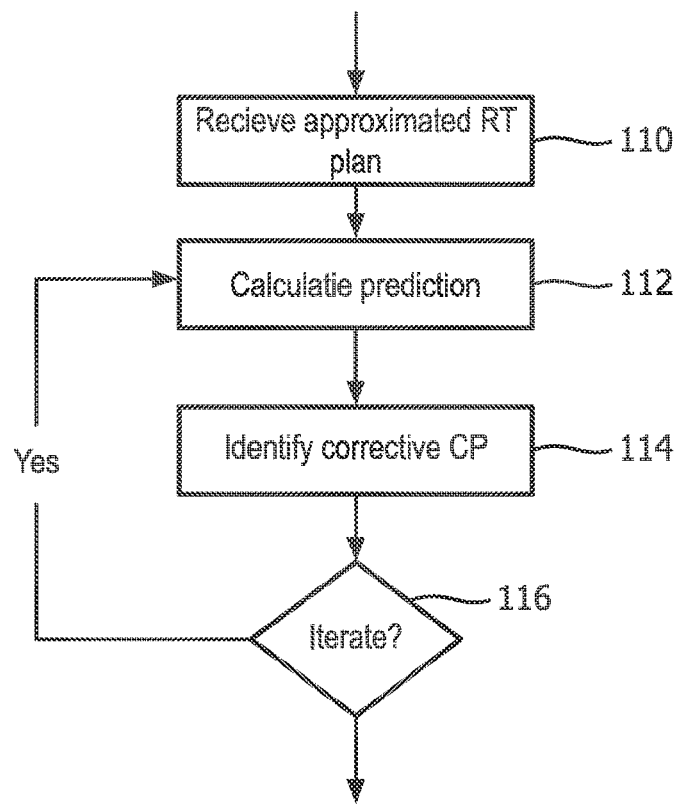

FIG. 5 flowcharts one embodiment of a method of iterative refinement of CPs in RT planning.

Figure 6:
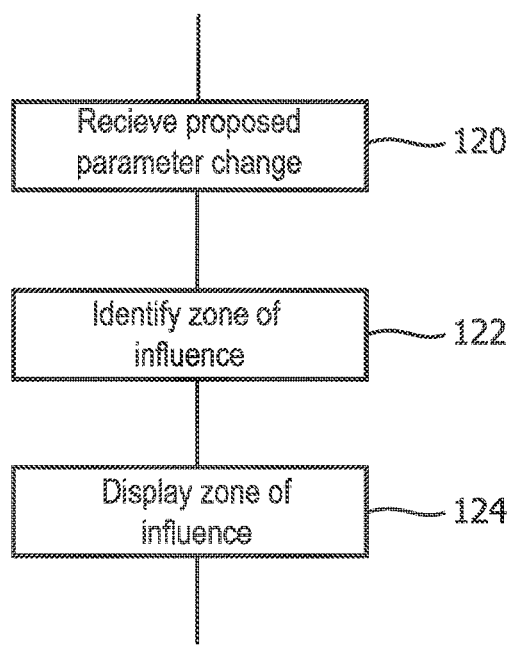

FIG. 6 flowcharts one embodiment of a method of visualizing a zone of influence.

Figure 7:
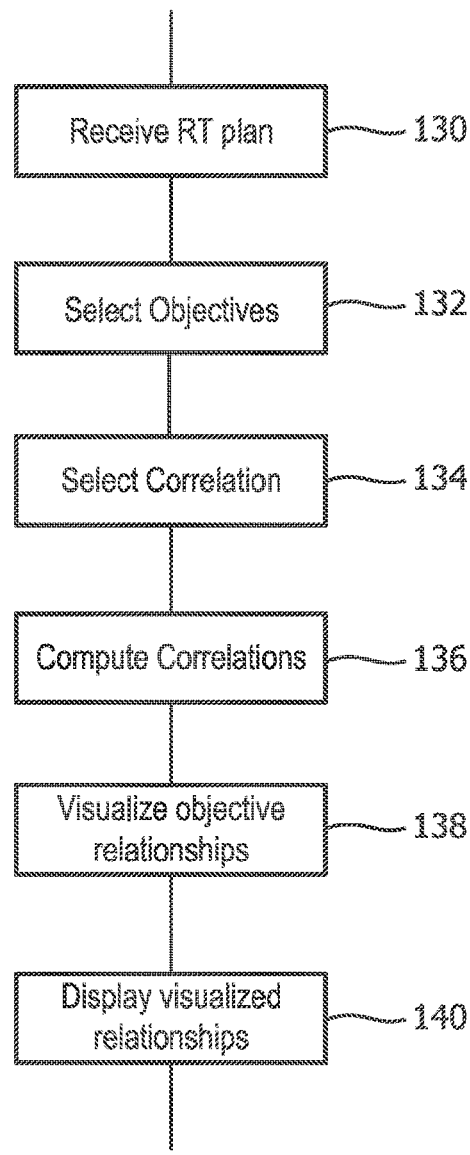

FIG. 7 flowcharts one embodiment of a method of visualizing RT plan objective relationships.

Figure 1:
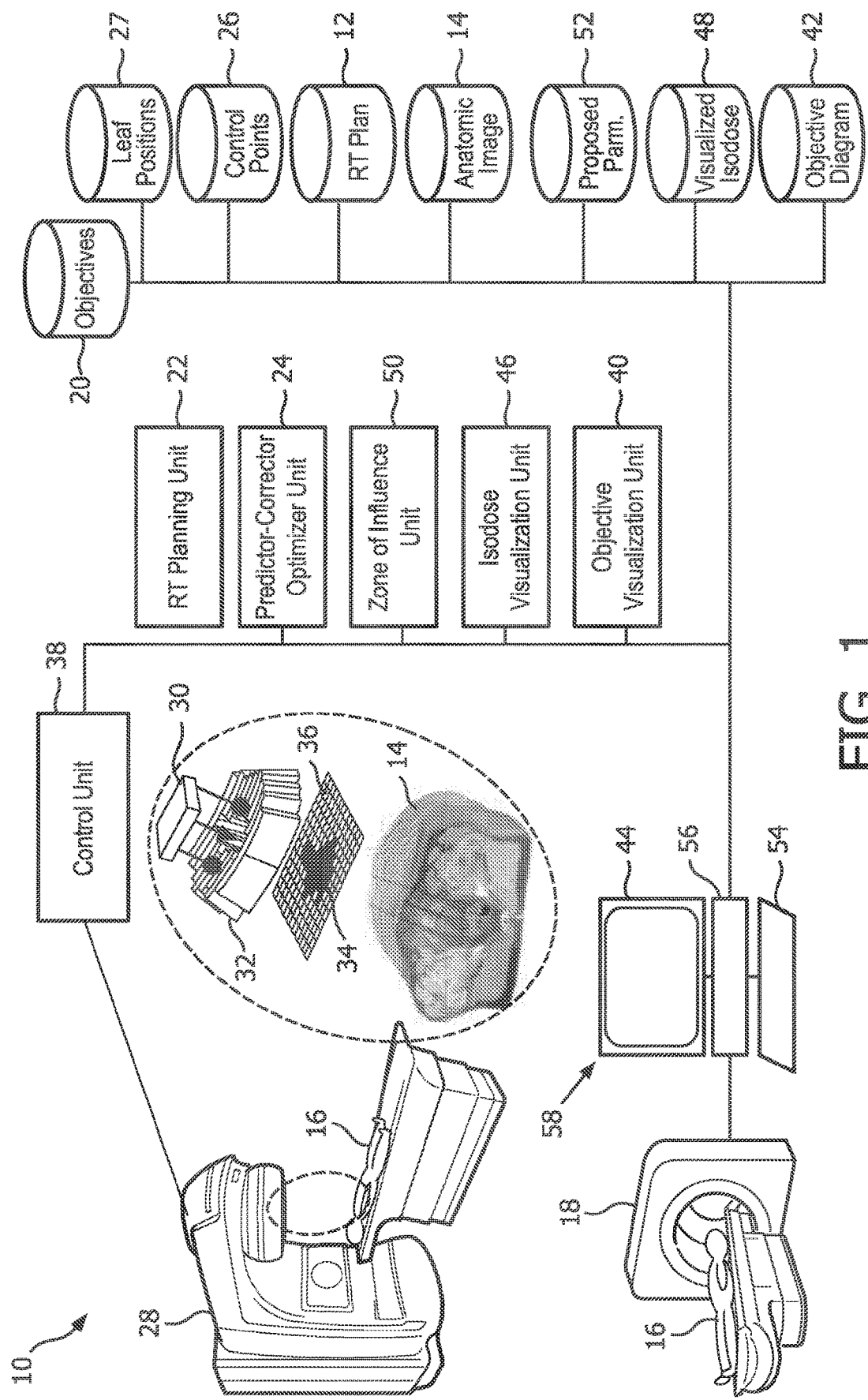

With reference to FIG. 1, an embodiment of a radiation delivery planning optimization and visualization system 10 is schematically illustrated with an exploded view of radiation delivery. A radiation therapy (RT) or radiation delivery plan 12 is constructed based on an anatomical or internal planning image 14 of a subject 16 acquired from an imaging device 18, such as a CT imaging device, MRI imaging device, and the like. The planning image 14 identifies regions of interests (ROIs), which includes the boundaries of one or more targets and OARs, and is used to determine a three dimensional density distribution that allows computing dose. RT plan objectives 20 can reference or store the ROIs, weights, and other objective type specific parameters like a reference dose, as input parameters to an inverse planning unit or means 22, which creates a RT plan.

Within the RT planning unit 22, a predictor-corrector optimizer unit or means 24 receives the plan objectives, a set of control points 26 and the current dose, $d_{curr}$, calculated by a dose engine. A predicted set of fluence plane values $x^*$ is determined, in a formal parameter space based on a set of CPs. The optimizer unit uses a gain function of the form, $\|x^*-x_{curr}-\gamma s\|^2-\|x^*-x_{curr}\|^2$, to identify a new set of leaf positions s with a weight $\gamma$ 27 using a layered graph structure with a shortest path solver. The predictor-corrector optimizer unit iterates creating new or refined control points with leaf positions until a user stopping criterion is reached, such as a maximum number of iterations, a minimum difference improvement in the objective function, a maximum computation time or a maximum number of control points is achieved. The predictor-corrector optimizer unit outputs the RT plan with set of CPs to the RT plan data store 12, such as a computer memory, a file in a file system, an object in a database, and the like. The data store can be implemented with random access memory such as solid state, hard disk, optical media, and the like.

The control points are control points of a radiation delivery device or means 28, such as a linear accelerator (LINAC) shown with an exploded view of the radiation source 30 relative to a portion of the subject anatomy 14. The radiation delivery device includes jaws and a multi-leaf collimator 32 with pairs of positionable leaves. The opening, through which the radiation passes, forms an illumination pattern 34 in a discrete fluence plane 36. The control points collectively, each with a set of leaf positions, form control instructions which operate a controller unit or means 38 to deliver the external beam of radiation of shapes and positions defined by the RT plan to tissues or internal regions 14 of the subject 16.

A smoother segment shape, such as more rectangular, results in less uncertainty in the dose computation. A larger segment opening results in a plan with a smaller total energy transmitted by the machine (Monitor Units). A higher efficiency of the energy, smaller total Monitor Units, has typically less (leakage) dose to organs at risks, quicker to deliver, and dose can be computed with higher accuracy. Variation in weights between control points can be a consideration with VMAT plans. In VMAT, the machine irradiates while the machine continuously varies between control points. Less variation in control point weights makes the dose easier to approximate. In one embodiment, the consecutive redetermination of the leaf positions for some of the control points can be part of an optimization routine, for instance DMPO or VMAT. It can also be part of a plan adaptation strategy, where the plan coming in was created using different shapes of the regions of interest and density information of the patient than used during the redetermination of segment shapes. In that context, the limitation of the segment shape to those similar to the original shape can have an advantage beyond computational efficiency that the plan needs less reviewing, typically by a physician, after adaptation.

An objective visualization unit or means 40 receives the RT plan with objectives, computes correlations of gradients of the objectives or plan parameters, and constructs a diagram 42 such as a graph or pivot table, which visualizes the correlation between objectives. For example, an overview of the correlations can be represented by a pivot table. The constructed diagram is displayed on a display device 42, such as one or more of a LCD display, an LED display, a plasma display, a projection display, a touch screen display, and the like. The displayed diagram provides the planner with a visual representation of interplay between the various objectives. The displayed diagram includes indicators of the objectives or selected objectives, and connectors indicative of the type and size of the correlation. The connectors include a sign, e.g. positive or negative correlation, and a magnitude or size of the correlation.

The objective visualization unit 40 correlates by a gradient of the plan objectives with respect to dose described by a correlation function $$c(\theta_0, i, j) = C\left(\frac{\partial O_i}{\partial d}, \frac{\partial O_j}{\partial d}\right)$$

where $\theta_0$ are current parameter values, $O_i$ and $O_j$ are parameters of ith and jth objectives respectively, and d are the dose volume values.

In another embodiment the objective visualization unit 40 correlates by a gradient of the plan objectives with respect to parameters of an optimization problem such as intensity values of pixels in fluence planes or leaf positions in direct machine parameters described by a correlation function $$c(\theta_0, i, j) = C\left(\frac{\partial O_i}{\partial x}\frac{\partial x}{\partial \theta}, \frac{\partial O_j}{\partial x}\frac{\partial x}{\partial \theta}\right) = C\left(\frac{\partial O_i}{\partial \theta}, \frac{\partial O_j}{\partial \theta}\right)$$

where $\theta$ is a parameter of a RT plan.

In one embodiment, the diagram includes a CT image or dose volume representation. In another embodiment, the diagram includes interactive features selected by the planner using the input device. The correlations are indicated with a color and/or texture shading according to the correlated values. For example, a sum of selected objectives $\Sigma_i O_i$ at the current values of the parameters $\theta_0$, where O is a vector with contribution to the objective value per dose voxel, visualizes a contribution per voxel to the selected objectives which can be indicated on the CT image and/or dose volume representation. The planner selects the objectives and an option to visualize the contribution per voxel. In another example, a sum of derivatives of selected objectives $$\sum_i \frac{\partial O_i}{\partial d}$$

at the current values $\theta_0$ of the parameters, visualizes the voxels of the dose volume contributing to the objective value and a sensitivity of the objective on the dose in each voxel. The planner selects objectives and an option to visualize the contributing voxels of the dose volume. In a third example, a sum of the derivatives of selected parameters $$\sum_j \frac{\partial d}{\partial \theta_j}$$

visualizes an expected dose change as the values of the selected parameters are varied. The planner selects the parameters such as fluence pixels or leaf positions, and an option to visualize the expected dose change. In a fourth example, a sum of the derivatives of selected objectives is multiplied with a dose per parameter of selected parameters $$\sum_{i,j} \frac{\partial O_i}{\partial d} \frac{\partial d}{\partial \theta_j} \left(\frac{\partial d}{\partial \theta}\right)^T$$

where T denotes the matrix transpose, to analyze the relation between the selected parameters and the selected objectives. In a fifth example, two selected sets i and j of objectives are correlated in the dose space $$\sum_{i,j} C\left(\frac{\partial O_i}{\partial d}, \frac{\partial O_j}{\partial d}\right).$$

In a sixth example, a correlation of the derivatives of two selected sets i and j of objectives $$\sum_{i,j} C\left(\frac{\partial O_i}{\partial p}, \frac{\partial O_j}{\partial p}\right)\left(\frac{\partial d}{\partial p}\right)^T$$

visualizes changes to a set of parameters scaled with the dose. In a seventh example, a correlation of the derivations of a set of selected objectives $$\sum_i C\left(\frac{\partial O_i}{\partial d}, \Delta d\right)$$

visualizes a dose change $\Delta d$ due to target and/or patient motion.

An isodose visualization unit or means 46 visualizes the planned doses of the current RT plan superimposed on the planning image 14. For example, an anatomical image is displayed on the display device 44 to the planner with isodose curves 48 indicative of the planned dose level from the current RT plan superimposed on the anatomical image. ROI boundaries can be further indicated on the planning image.

A zone of influence unit or means 50 receives a proposed parameter change 52 to the objectives of the current RT plan from the planner using an input device 54, such as one or more of a mouse, a keyboard, a touch screen display, one or more buttons, one or more switches, one or more toggles, and the like. The current RT plan has an objective function $O(d_{curr}; \theta)$ where $\theta$ is a RT plan parameter with a current value of $\theta_0$, and the objective function is optimized over the current approximate dose or fluence. The zone of influence unit identifies a zone of influence in the dose space from the change in the parameter based on a function $$\frac{\partial O(d_{curr}; \theta = \theta_0)}{\partial \theta}$$

where d are the values of the voxels in the dose volume, e.g. current approximate dose at all locations. The evaluation of the function provides the changes to dose in the dose space which are mapped to the anatomical or planning space. For example, the voxels for which the dose changes based on evaluation of the function are identified. The zone of influence unit constructs a visual representation of the zone of influence superimposed on the planning image 14. The visualized zone of influence superimposed on the planning image is displayed on the display device 44. In one embodiment, the display includes the image with isodose curves constructed by the isodose visualization unit 46. In another embodiment, magnitudes of the changes in dose are indicated visually.

The zone of influence unit 50 interactively receives a change to individual parameters and visualizes the change to the planner, which allows the planner to understand the potential impact of the parameter change, and to select a parameter change which provides the most beneficial or best RT plan. The selected parameter is then re-input to the RT planning unit 22 and the predictor-corrector optimizer unit 24 which revises the RT plan. With each revision of the RT plan, the planner can visualize potential parameters changes as a next step with the zone of influence unit 50 and review the relationship between the objectives with the objective visualization unit 40. Parameter changes can include changes to objective parameters like the weight and reference dose.

The various units 22, 24, 38, 40, 46, 50 are suitably embodied by a computer or data processing device, such as an electronic processor or electronic or optical processing device 56 of a workstation 58, or by a network-based server computer operatively connected with the workstation 58 by a network, Field Programmable Gate Array (FPGA), Application Specific Integrated Chip (ASIC), mechanical or fluid computing or calculating machine, physical simulation of a Turing machine, or so forth. Moreover, the disclosed RT planning, optimization and visualization techniques are suitably implemented using a non-transitory storage medium storing instructions (e.g., software) readable by an electronic data processing device and executable by the electronic data processing device to perform the disclosed techniques.

Figure 2:
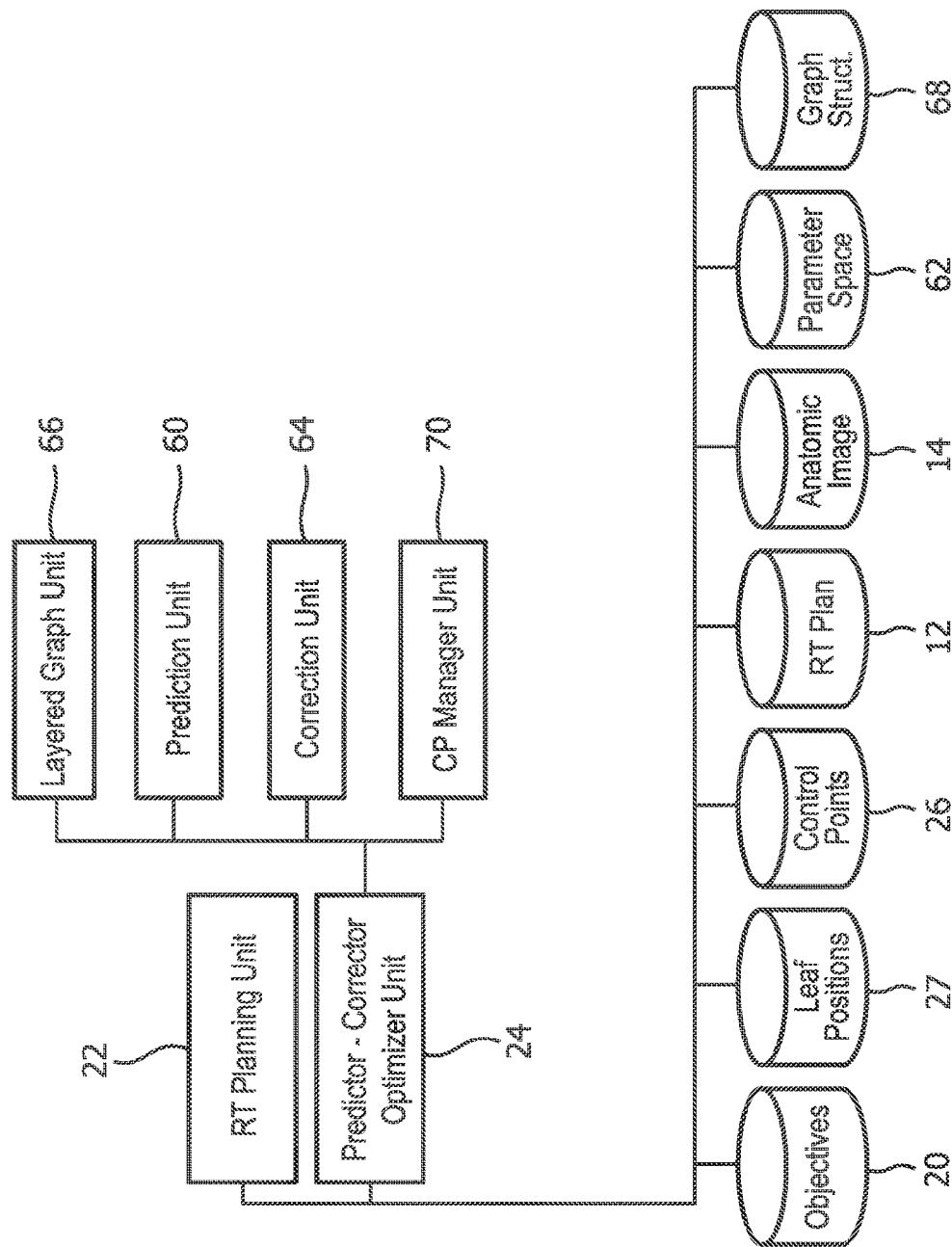

With reference to FIG. 2, one embodiment of the predictor-corrector optimizer unit 24 is schematically illustrated. The predictor-corrector optimizer unit 24 includes a prediction unit 60 configured to receive the radiation therapy plan which includes the current dose, and a collection of CPs 26, each CP with a corresponding set of leaf positions 27 for the MLC that form an approximate set of discrete fluence planes values $x_{curr}$ 36 and calculate the dose $d_{curr}$ in the formal parameter space 62. One method to map the approximated discrete fluence maps $x_{curr}$ to dose is with a fluence dose contribution matrix P. For each CP, a non-negative mapping exists from the set of MLC leaf positions 27 to the dose volume d. Each CP includes attributes of a positive weight $\gamma$ and a set of leaf positions s. The set of leaf positions define ray blocking and passing regions represented with a function $x_i$ where the function is 1 in a passing region and 0 in a blocked region. Thus, for each beam position the current approximate fluence plane is defined by $$x_{curr} = \sum_i \gamma_i \sum_j \chi_{i,j},$$

where $\gamma_i$ is the positive weight of control point i, and $x_j$ is the passing function for each jth position or pixel of the fluence plane as used in Fluence Map Optimization (FMO). The prediction unit 60 calculates the predicted fluence planes values x* and with the corresponding dose d the objective function using $x^* = \mathrm{argmin}_{x \geq x_{curr}} \Sigma_j \alpha_j O_j(d)$, value. In FMO, a nonlinear optimization algorithm, such as a Broyden-Fletcher-Goldfarb-Shannon algorithm, optimizes the parameters x to minimize the objective function value O.

A correction unit or computing device 64 is configured to determine an additional control point with a corresponding set of leaf positions by a corrective mapping of a difference of the current approximate fluence plane values resulting from the current set of control points at that beam position and the ideal fluence plane values obtained for instance using a FMO routine, $x^* - x_{curr}$ through a least cost or shortest path in a layered graph structure of leaf positions for each potential CP. The layered graph uses a cost function defined by $\|x^* - x_{curr} - \gamma s\|^2 - \|x^* - x_{curr}\|^2$, where $\gamma$ represents an unknown weight and s represents an unknown set of leaf positions. The cost function can be expanded to include other preferences like segment shape, segment opening, and variation in weights between control points.

A layered graph unit or computing device 66 constructs a layered graph structure 68 for all possible positions of the leaves in the MLC for each potential CP. The layered graph structure with possible MLC leaf positions is more fully explained in European provisional patent application "Device for determining illumination distributions for IMRT" Serial No. EP 13169709.6 filed 29.05.13. The layered graph is applicable to static and dynamic beam settings, e.g. DMPO and VMAT. The layered graph structure includes layers with nodes for each pair of positions for a pair of leafs. The layers represent all the leaf pairs, e.g. a layer for each leaf pair Each $i^{th}$ layer represents a leaf pairs in the $i^{th}$ row of a multi-leaf collimator (MLC). The nodes of each layer represent realizable leaf pair positions. Each node is represented by a vector $b_r$ which includes a binary sequence where each bit represents a pixel or opening with a value of 1 for passing and 0 for blocked. Nodes of adjacent layers are connected by graph edges to which first weights $e_r$ and regularization values are assigned. A fluence map gradient based objective function is used to calculate the edge weights. In one embodiment, a plurality of mappings or shortest paths are determined with the layered graph structure, each determining a CP, and a best CP is selected from the CPs according to a predetermined metric.

A CP manager unit or computing device 70 adds the additional or selected CP with corresponding set of leaf positions to the collection of CPs 26. The predictor-corrector optimizer unit 24 iteratively invokes the prediction unit 60 and the correction unit 64 until the user stopping criteria is met. The collection of CPs with corresponding set of leaf positions form the revised RT plan 12. In one embodiment, one of the CPs is removed from the collection before calculating the approximate fluence plane values. In another embodiment, the leaf positions of a new control point are determined.

Figure 3:
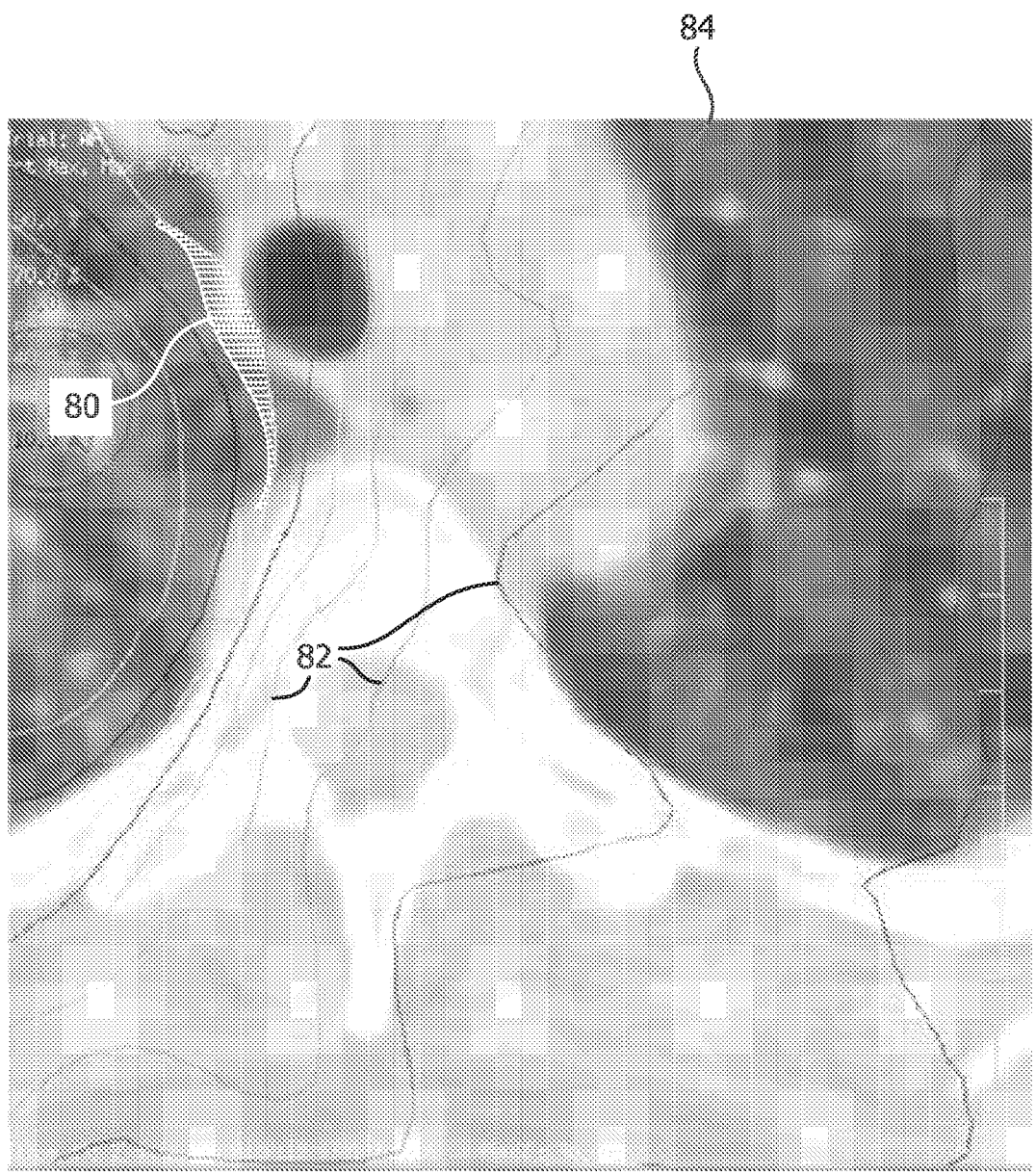
FIG. 3 illustrates an exemplary of a visualized zone of influence.

With reference to FIG. 3, an exemplary of a visualized zone of influence 80 is illustrated superimposed on a display of isodose curves 82 and an exemplary anatomical image 84. The anatomic image is a 2D CT image slice. Isodose curves are lines which delineate the planned dose. The lines can be indicated in color or otherwise contrasted with the anatomic image. The zone of influence is spatially indicated with a pattern, texture, and/or color in contrast to the anatomic image and isodose curves. Based on the visualize zone of influence and the selected parameter, the planner can decide whether to accept the parameter change and revise the RT plan based on the parameter change or select another parameter. The zone of influence can include spatially separated regions. In one embodiment, zones of influence can be preserved from one parameter change to another, and a visual comparison made of each preserved zone of influence. Color labeling or other identification is used to identify each zone of influence. The visualization is interactive between the planner and the system. The planner selects the changes in parameters values, which determine a zone of influence, and further selects which parameter changes are visualized.

Figure 4:
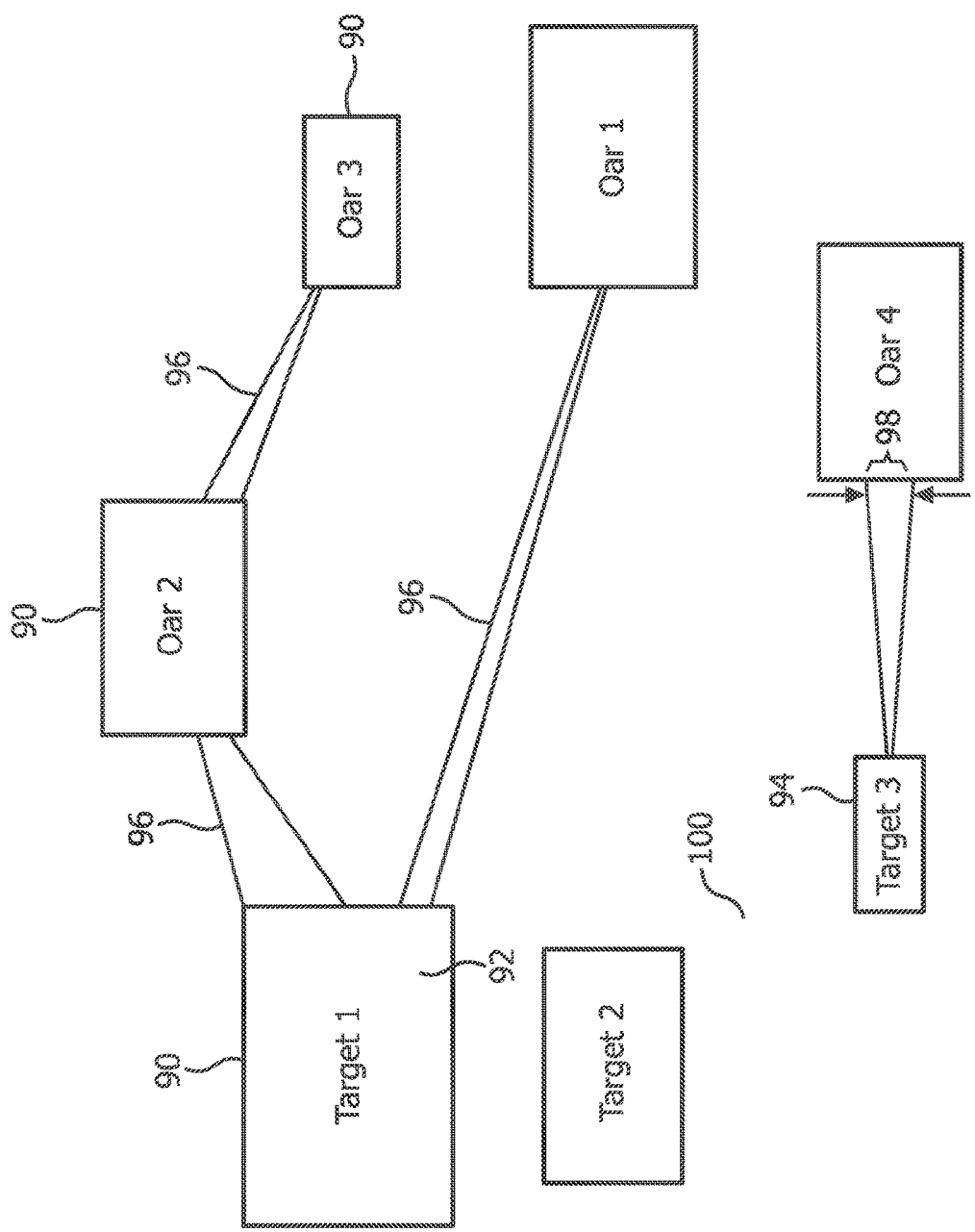
FIG. 4 illustrates an exemplary of a visualized objective correlation diagram.

With respected to FIG. 4, an exemplary of a visualized objective correlation diagram is illustrated. The diagram includes indicators of objective ROIs 90 which are represented as rectangles. The objective ROIs include targets and/or OARs. The objective rectangles are sized according to the influence of each objective on the sum of objective values. For example, "Target 1" 92 is the largest rectangle which contributes proportionally more to the sum of objective values than other indicated objectives, and "Target 3" 94 is the smallest rectangle which contributes less proportionally to the sum of objective values than other indicated objectives. Indicators for objectives can alternatively include other shapes, colors, textures and the like. For example, targets are indicated with a first color and sized according to a sum of objective values for target objectives, and OARs are indicated with a second color and sized according to a sum of objective values for OAR objectives.

Connectors 96 connect the objectives and indicate the correlation between objectives. The correlations between objectives are represented as connecting lines of variable length and width. A connecting width 98 of the line indicates the magnitude of the correlation. A dotted line 100 indicates negatively signed correlation. In other embodiments of the objective visualization unit the connectors include indicators, such as different length, area, width, shape, color, texture, and the like. Alternative diagrams include different selected objective parameters such as ROIs, weights, and doses. The alternative diagrams can include different correlated aspects of objectives parameters as in the examples discussed in reference to FIG. 1 and the objective visualization unit 40. The objectives or subsets of objectives can be interactively selected. The diagram can be filtered by the magnitude of the correlations, the number of connectors, and/or objective, such as objective parameter values and/or type of ROI, e.g. target or OAR.

With reference to FIG. 5, one embodiment of a method of iterative refinement of CPs in RT planning is flowcharted. In a step or by a module 110 an approximated radiation therapy (RT) plan is received. The RT plan includes a current approximate dose, $d_{curr}$, and a collection of control points. Each control point includes a corresponding set of leaf positions of a multi-leaf collimator. The set of leaf positions approximate a discrete fluence planes values, $x_{curr}$.

A predictive set of fluence planes values $x^*$ is calculated in a step or by a module 112. The discrete fluence maps are based on each CP in the collection. In one embodiment one of the CPs in the collection is selected and removed before calculating the approximate fluence planes values. The selection can include an ordered selection in each iteration such that each of the CPs are removed over the iterations, e.g. one CP for each iteration and iterations over the collection of CPs.

An additional control point with a corresponding set of leaf positions is determined in a step or by a module 114. The additional CP is determined by a corrective mapping of a difference of the current approximate fluence and the predictive fluence, $x^*-x_{curr}$. The mapping is through a least cost or shortest path in a layered graph structure of leaf positions for each potential CP. The additional CP with corresponding set of leaf positions is added to the collection of CPs, which forms the collection of CPs for the next iteration.

In a step or by a module 116 steps are repeated until a predetermined stopping criterion is met. For example, the stopping criteria can include a number of iterations and/or a threshold change in the difference of the current objective function value. It is to be appreciated that although described in terms of radiation therapy, the method is also applicable to planning irradiation for various industrial, manufacturing, and other uses in which inanimate objects are irradiated with a selected radiation beam.

With reference to FIG. 6, one embodiment of a method of visualizing a zone of influence is flowcharted. In a step or by a module 120, a change in a radiation plan parameter θ with current parameter values $θ_0$ in an objective function O(d; θ) is received. The value is received from an input device. The parameter value is a value of a radiation therapy plan which includes a dose space and a plurality of plan objective parameters such as regions of interest, dose levels, and relative weights of objectives. The objective function O is optimized over the fluence or dose.

A zone of influence in the dose space is identified from the change in the parameter in a step or by a module 122 based on the function:

$$\frac{\partial O(d; \theta = \theta_0)}{\partial \theta}$$

where d is a dose volume. The zone of influence effect on at least one of the regions of interest is visualized. For example, a numerical representation and/or a highlighted spatial location of the zone of influence effect indicated on one or more ROIs. In another embodiment the visualization includes a tabular display of dosimetric measures of the zone of influence effect.

In a step or by a module 124, the visual representation of the zone of influence is displayed. The display can include the visualized representation superimposed on a display of isodose curves and a planning image and/or ROI. The display can include the tabular display. The display can be limited to one or more of the ROIs.

With reference to FIG. 7, one embodiment of a method of visualizing RT plan objective relationships is flowcharted. In a step or by a module 130, a radiation therapy plan is received which includes the current dose or the dose voxels d, and the plan objectives.

In a step or by a module 132, one or more sets of plan objectives or plan parameters are selected. For example, all plan objectives can be selected as a default setting.

In another example, one or more subsets of plan objectives are selected interactively by the planner as discussed in reference to FIG. 1 and the objective visualization unit 40.

The type of correlation is selected in a step or by a module 134. The correlation type can include how the selected objectives or parameters are to be correlated. For example, one correlation between objectives can include a gradient of the plan objectives with respect to dose and a function $$c(\theta_0, i, j) = C\left(\frac{\partial O_i}{\partial d}, \frac{\partial O_j}{\partial d}\right)$$

where $\theta_0$ are current parameter values, $O_i$ and $O_j$ are objectives respectively, and d is the dose volume. In another example, the correlation includes a gradient of the plan objectives with respect to parameters of an optimization problem such as intensity values of pixels in fluence planes or leaf positions in direct machine parameters and a function $$c(\theta_0, i, j) = C\left(\frac{\partial O_i}{\partial d}\frac{\partial d}{\partial \theta}, \frac{\partial O_j}{\partial d}\frac{\partial d}{\partial \theta}\right) = C\left(\frac{\partial O_i}{\partial \theta}, \frac{\partial O_j}{\partial \theta}\right)$$

where $\theta$ are parameters of an optimization problem. Other examples are discussed in reference to FIG. 1 and the objective visualization unit 40. The correlation is computed in a step or by a module 136 with the selected correlation type and selected objectives and/or parameters.

The computed correlations and selected objectives are visualized in a diagram constructed in a step or by a module 138. The diagram can include a graph or pivot table which visualizes the correlation either spatially and/or numerically. For example, the diagram includes a first indicator type for each plan objectives, such as a rectangle sized relative to an influence of each objective on a sum of objective values, and a second indicator type for each correlation, such as a line connecting between the correlated objectives sized and shaped relative to the sign and magnitude of the correlation. The visualized diagram is displayed on a display device in a step or by a module 140.

The method steps are contemplated for the application of external beams of radiation to selected regions of objects which include a defined portion to receive at least a desired level of radiation exposure and other defined portions which receive a minimized dose. For example, surfaces of food items and/or food packaging are irradiated while minimizing irradiating the food items. In another example, cross-linked polymers formed by irradiation can be formed in precise shapes with the selective application of the radiation beams to a pre-cross linked polymer solution, e.g. tubing formation.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular units, means, elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A method of radiation delivery planning, the method comprising:

receiving a radiation delivery plan comprising a collection of control points, each control point having a corresponding set of leaf positions for a multi-leaf collimator that define a current approximate fluence plane value ($x_{curr}$);

determining a predictive set of fluence plane values ($x^*$) with a corresponding dose volume by removing one of the control points from the collection of control points before determining the current approximate fluence plane value and dose; and determining an additional control point with a corresponding set of leaf positions by a corrective mapping of a difference of the current approximate fluence plane value ($x_{curr}$) and the predictive set of fluence plane values ($x^*-x_{curr}$) through a least a cost or a shortest path in a layered graph structure of leaf positions for each potential control point, and adding the determined additional control point with corresponding set of leaf positions to the collection of control points.

2. The method according to claim 1, further comprising: iterating the method until a number of iterations is met and/or a threshold change in the difference of a current approximate dose and a predictive dose is met.

3. The method according to claim 1, wherein the predictive set of fluence plane values ($x^*$) are determined by minimizing the function $$x^* = \operatorname*{argmin}_{x \geq x_{curr}} \sum_j \alpha_j O_j(Dx),$$

where x is the current approximate fluence plane value, $O_j$ is a $j^{th}$ dose objective, and α is a weight of an objective.

4. The method according to claim 1, wherein the shortest path is represented by a cost function defined by $\|x^*-x_{curr}-\gamma s\|^2-\|x^*-x_{curr}\|^2$, where γ represents an unknown weight and s represents an unknown set of leaf positions, wherein the cost function can be expanded to comprise a segment shape, a segment opening, and a variation in weights between control points.

5. The method according to claim 1, wherein the layered graph structure is limited to control points within a vicinity of the removed control point.

6. The method according to claim 1, wherein the corrective mapping comprises a plurality of corrective mappings each yielding a control point; and
wherein the adding comprises a selection of one of the determined control points according to a predetermined metric.

7. The method according to claim 1, wherein the layered graph structure comprises layers with nodes for each potential control point, and each $i^{th}$ layer represents a leaf pairs in an $i^{th}$ row of a multi-leaf collimator (MLC), and the nodes in a layer represent all realizable leaf pair positions and each node represented by a vector $b_r$ which comprises a binary sequence where each bit represents a pixel or opening with a value of 1 for non-collimated and 0 for collimated, and nodes of adjacent layers are connected by graph edges to which first weights $e_r$ and regularization values are assigned.

8. The method according to claim 1, wherein the current approximate fluence plane value, $x_{curr}$, is defined by $$x_{curr} = \sum_i w_i \chi_i,$$

where w is a weight, x is a characteristic function with 1 in a passing position and 0 in a blocked position, and summed for each control point i.

9. A non-transitory computer-readable storage medium that stores instructions, which when executed by a processor, cause the processor to perform the method according to claim 1.

10. The method according to claim 3, wherein the $x^*$ is computed with a nonlinear optimization algorithm.

11. The method according to claim 10, wherein the nonlinear optimization algorithm is a Broyden-Fletcher-Goldfarb-Shannon algorithm comprising a limited memory variant.

12. A system for radiation delivery planning, comprising:
a control point manager unit configured to receive a radiation delivery plan which comprises a current approximate dose ($d_{curr}$), and a collection of control points, each control point having a corresponding set of leaf positions for a multi-leaf collimator that define a current approximate fluence plan value ($x_{curr}$);
a prediction unit configured to determine a predictive set of fluence plane values ($x^*$) with a corresponding dose volume by removing one of the control points from the collection of control points before determining the current approximate fluence plane value and dose, wherein the predictive set of fluence plane values ($x^*$) map to a parameter space with a dose matrix d; and
a correction unit configured to determine an additional control point with a corresponding set of leaf positions by a corrective mapping of a difference of the current approximate fluence plane values and the predictive fluence values ($x^*-x_{curr}$) through a least cost or shortest path in a layered graph structure of leaf positions for each potential control point, wherein an additional control point manager unit is further configured to add the determined control point with corresponding set of leaf positions to the collection of control points.

13. A radiation delivery system comprising:
a radiation delivery device;
a controller configured to control the radiation delivery device to deliver radiation pursuant to a radiation delivery plan, the controller comprising: a memory that stores instructions; and a processor that executes the instructions, wherein when executed by the processor, the instructions cause the controller to:
receive a radiation delivery plan comprising a collection of control points, each control point having a corresponding set of leaf positions for a multi-leaf collimator that define a current approximate fluence plane value ($x_{curr}$);
determine a predictive set of fluence plane values ($x^*$) with a corresponding dose volume by removing one of the control points from a current collection of control points before determining the current approximate fluence plane and dose; and
determine an additional control point with a corresponding set of leaf positions by a corrective mapping of a difference of the current approximate fluence plane values ($x_{curr}$) and the predictive set of fluence plane values, $x^*-x_{curr}$ through a least a cost or a shortest path in a layered graph structure of leaf positions for each potential control point, and adding the determined additional control point with corresponding set of leaf positions to the collection of control points.

14. The radiation delivery system of claim 13, wherein the shortest path is represented by a cost function defined by $\|x^*-x_{curr}-\gamma s\|^2-\|x^*-x_{curr}\|^2$, where γ represents an unknown weight and s represents an unknown set of leaf positions, wherein the cost function can be expanded to comprise a segment shape, a segment opening, and a variation in weights between control points.

15. The radiation delivery system of claim 13, wherein the layered graph structure is limited to control points within a vicinity of the removed control point.

16. The radiation delivery system of claim 13, wherein the corrective mapping comprises a plurality of corrective mappings each yielding a control point; and wherein the adding comprises a selection of one of the determined control points according to a predetermined metric.

17. The radiation delivery system of claim 13, wherein the layered graph structure comprises layers with nodes for each potential control point, and each $i^{th}$ layer represents a leaf pairs in an $i^{th}$ row of a multi-leaf collimator (MLC), and the nodes in a layer represent all realizable leaf pair positions and each node represented by a vector $b_r$ which comprises a binary sequence where each bit represents a pixel or opening with a value of 1 for non-collimated and 0 for collimated, and nodes of adjacent layers are connected by graph edges to which first weights $e_r$, and regularization values are assigned.

* * * * *